United States Patent [19]

Hindley

[11] Patent Number: 5,063,240

[45] Date of Patent: Nov. 5, 1991

[54] NOVEL COMPOUNDS

[75] Inventor: Richard M. Hindley, Epsom, England

[73] Assignee: Beecham Group p.l.c., Brentford, United Kingdom

[21] Appl. No.: 521,157

[22] Filed: May 7, 1990

[30] Foreign Application Priority Data

May 9, 1989 [GB] United Kingdom ............. 8910639

[51] Int. Cl.$^5$ ............. C07D 417/12; A61K 31/425
[52] U.S. Cl. ............................. 514/369; 548/183
[58] Field of Search ................... 548/183; 514/369

[56] References Cited

U.S. PATENT DOCUMENTS 4,725,610  2/1988  Meguro ........................ 514/369
4,918,091  4/1990  Cantello ....................... 514/369

*Primary Examiner*—Robert Gerstl
*Attorney, Agent, or Firm*—Hopgood, Calimafde, Kalil, Blaustein & Judlowe

[57] ABSTRACT

A compound of formula (I):

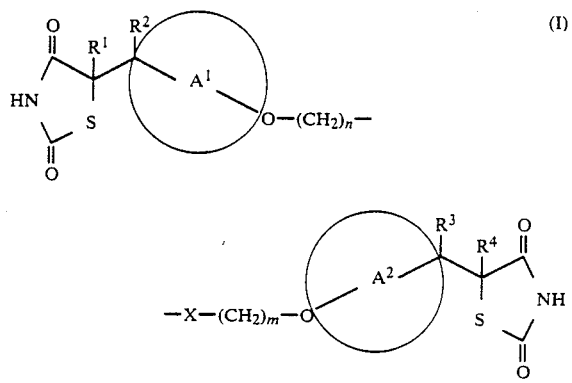

or a tautomeric form thereof and/or a pharmaceutically acceptable salt thereof and/or a pharmaceutically acceptable solvate thereof, characterized in that:

$R^1$ represents hydrogen, alkyl, aralkyl or aryl and $R^2$ represents hydrogen or $R^1$ and $R^2$ together represent a bond;

$R^3$ represents hydrogen and $R^4$ represents hydrogen, akyl, aralkyl or aryl or $R^3$ and $R^4$ together represent a bond;

X represents a bond, >C=O, >CHOH, O, S or NR wherein R is an alkyl group;

n represents an integer 1, 2 or 3;

m represents an integer 1, 2 or 3 and $A^1$ and $A^2$ each independently represent a benzene ring having a total up to 5 substituents comprising up to 3 optional substituents; a process for preparing such a compound, a pharmaceutical composition comprising such a compound and the use of such compounds and compositions in medicine.

10 Claims, No Drawings

NOVEL COMPOUNDS

This invention relates to certain substituted thiazolidinedione derivatives, to a process for preparing such compounds, to pharmaceutical compositions containing such compounds and to the use of such compounds and compositions in medicine.

European Patent Applications, Publication Numbers 0008203, 0139421, 0155845, 0177353, 0193256, 0207581 and 0208420 relate to thiazolidinedione derivatives which are disclosed as having hypoglycaemic and hypolipidaemic activity. Chem. Pharm. Bull 30 (10) 3580-3600 also relates to certain thiazolidinedione derivatives having hypoglycaemic and hypolipidaemic activities.

It has now surprisingly been discovered that certain novel substituted-thiazolidinedione derivatives show improved blood-glucose lowering activity and are therefore of potential use in the treatment and/or prophylaxis of hyperglycaemia and are of particular use in the treatment of Type II diabetes.

These compounds are also indicated to be of potential use for the treatment and/or prophylaxis of other diseases including hyperlipidaemia, hypertension, cardiovascular disease and certain eating disorders.

Accordingly, the present invention provides a compound of formula (I):

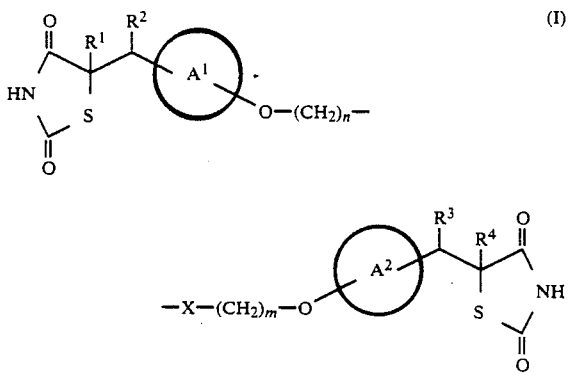

or a tautomeric form thereof and/or a pharmaceutically acceptable salt thereof and/or a pharmaceutically acceptable solvate thereof, wherein:

$R^1$ represents hydrogen, alkyl, aralkyl or aryl and $R^2$ represents hydrogen or $R^1$ and $R^2$ together represent a bond;
$R^3$ represents hydrogen and $R^4$ represents hydrogen, alkyl, aralkyl or aryl or $R^3$ and $R^4$ together represent a bond;
X represents a bond, $>C=O$, $>CHOH$, O, S or NR wherein R is an alkyl group;
n represents an integer 1, 2 or 3;
m represents an integer 1, 2 or 3 and
$A^1$ and $A^2$ each independently represent a benzene ring having a total up to 5 substituents comprising up to 3 optional substituents.

Suitably, $R^1$ and $R^2$ each represent hydrogen
Suitably, $R^3$ and $R^4$ each represent hydrogen
Suitably, X represents O, S or NR.
Preferably, X represents a bond.
Suitably, when X represents a bond, (n+m) represents an integer 2,3,4,5 or 6.
When $R^2$ is hydrogen and $R^1$ is not hydrogen, then $R^1$ is suitably an alkyl group, for example a methyl group.
When $R^3$ is hydrogen and $R^4$ is not hydrogen, then $R^4$ is suitably an alkyl group, for example a methyl group.
Suitable $A^1$ represents a benzene ring having no optional substituent.
Suitably, $A^2$ represents a benzene ring having no optional substituent.

In one particular aspect the invention provides a compound of formula (IA)

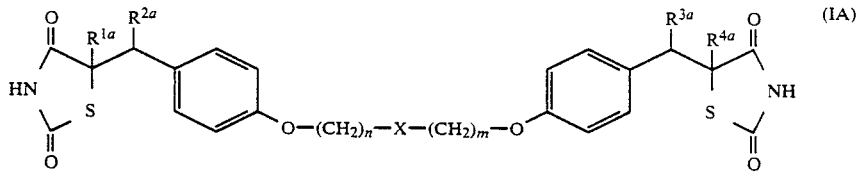

or a tautomeric form thereof and/or a pharmaceutically acceptable salt thereof and/or a pharmaceutically acceptable solvate thereof, wherein:

$R^{1a}$ and $R^{2a}$ each represent hydrogen or $R^{1a}$ and $R^{2a}$ together represent a bond;
$R^{3a}$ and $R^{4a}$ each represent hydrogen or $R^{3a}$ and $R^{4a}$ together represent a bond;
$X^1$ represents a bond, $>C=O$ or $>CHOH$;
n represents an integer 1, 2 or 3; and
m represents an integer 1, 2 or 3.

Suitable optional substituents for $A^1$ or $A^2$ include halogen, substituted or unsubstituted alkyl or alkoxy.

Suitable, favoured and preferred values for $R^{1a}$, $R^{2a}$, $R^{3a}$, $R^{4a}$ and $X^1$ are as defined herein for variables $R^1$, $R^2$, $R^3$, $R^4$ and X respectively.

As indicated above a compound of formula (I) may exist in one of several tautomeric forms, all of which are encompassed by the present invention. The present invention encompasses all of the isomeric forms of the compounds of formula (I) and the pharmaceutically acceptable salts thereof, including any stereoisomeric forms thereof, whether as individual isomers or as mixtures of isomers.

When used herein the term 'halogen' refers to fluorine, chlorine, bromine and iodine; preferably chlorine.

When used herein the terms 'alkyl' and 'alkoxy' relate to groups having straight or branched carbon chains, containing up to 12 carbon atoms.

Suitable alkyl groups are $C_{1-12}$ alkyl groups, especially $C_{1-6}$ alkyl groups e.g. methyl, ethyl, n-propyl, iso-propyl, n-butyl, isobutyl or tert-butyl groups.

Suitable substituents for any alkyl group include up to five, preferably up to three, groups selected from halogen, alkyl, phenyl, alkoxy, haloalkyl, hydroxy, amino, nitro, carboxy, alkoxycarbonyl, alkoxycarbonylalkyl, alkylcarbonyloxy, or alkylcarbonyl groups.

Suitable pharmaceutically acceptable salts include salts of the thiazolidinedione moiety, and, where appropriate, salts of carboxy groups.

Suitable pharmaceutically acceptable salts of the thiazolidinedione moiety include metal salts especially alkali metal salts such as the lithium, sodium and potassium salts.

Suitable pharmaceutically acceptable salts of carboxy groups include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Suitable pharmaceutically acceptable solvates include hydrates.

In a further aspect the present invention also provides a process for the preparation of a compound of formula (I), or a tautomeric form thereof and/or a pharmaceutically acceptable salt thereof and/or a pharmaceutically acceptable solvate thereof, which process comprises reacting a compound of formula (II):

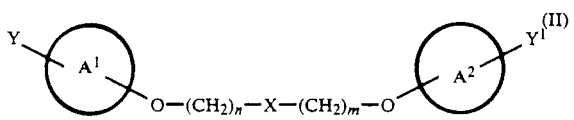

wherein n, m, $A^1$, $A^2$ and X are as defined in relation to formula (I), Y and $Y^1$ each independently represents —CHO or a moiety of formula (a):

providing that Y and $Y^1$ do not both represent the moiety of formula (a), with 2,4-thiazolidinedione; and thereafter, if required, carrying out one or more of the following optional steps:

(i) converting a compound of formula (I) into a further compound of formula (I);
(ii) preparing a pharmaceutically acceptable salt of the compound of formula (I) and/or a pharmaceutically acceptable solvate thereof.

The reaction between the compound of formula (II) and 2,4-thiazolidinedione may be carried out under any suitable conditions, the reaction being conveniently carried out in a solvent such as toluene, suitable at an elevated temperature, such as the reflux temperature of the solvent and preferably in the presence of a suitable catalyst such as piperidinium acetate or piperidinium benzoate. Favourably, in the reaction between the compound of formula (II) and 2,4-thiazolidinedione, the water produced in the reaction is removed from the reaction mixture, for example by means of a Dean and Stark apparatus.

A compound of formula (II), wherein Y or $Y^1$ represents a moiety of the above defined formula (a), may be prepared by reducing a compound of formula (III).

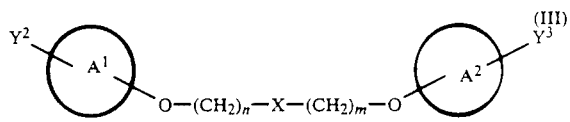

wherein n, m, $A^1$, $A^2$ and X are as defined in relation to formula (I), $Y^2$ represents —CHO or a protected form thereof or a moiety of formula (b):

and $Y^3$ represents —CHO or a protected form thereof or a moiety of the above defined formula (b) providing that one of $Y^2$ or $Y^3$ represents a moiety (b); and thereafter, if required, deprotecting a protected form of —CHO to provide the appropriate compound of formula (II).

The reduction of the compound of formula (III) may be carried out using any suitable reducing procedure which is capable of reducing the moiety (b) to the moiety (a) without reducing any keto moiety present in the compound of formula (III) and, preferably, without reducing any —CHO group.

Favourably, the reaction is carried out using catalytic reduction. Suitable catalysts for use in the catalytic reduction are palladium on carbon catalysts, preferably a 10% palladium on charcoal catalyst; the reduction being carried out in a solvent, for example dioxan, suitably at elevated temperature.

A compound of formula (III) may be prepared by reacting a compound of the above defined formula (II), wherein Y and $Y^1$ both represent —CHO, with one molar equivalent of thiazolidinedione and thereafter, if required, protecting any —CHO group in the resulting product.

The reaction between the said compound of formula (II) and 2,4-thiazolidinedione may be carried out under conditions analogous to those mentioned above in relation to the general reaction between a compound of formula (II) and 2,4-thiazolidinedione.

Suitable protected forms of a —CHO group include conventionally protected forms of the —CHO group, for example —CHO protected in the form of an acetal.

The methods of formation and removal of such protecting groups are those conventional methods appropriate to the molecule being protected. Thus for example an acetal group may be prepared by treatment of the appropriate aldehyde with a diol, such as ethane-1,2-diol, in acidic conditions and thereafter, when required, the acetal group may be removed, suitably by hydrolysis under mildly acidic conditions.

In an alternative aspect, the present invention provides a process for preparing a compound of formula (I), or a tautomeric form thereof and/or a pharmaceutically acceptable salt thereof and/or a pharmaceutically acceptable solvate thereof, which process comprises reacting a compound of formula (IV):

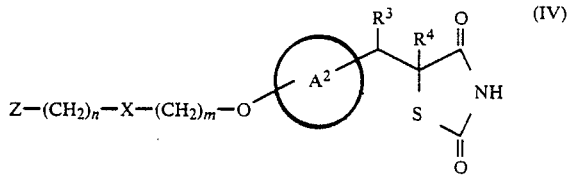

wherein $R^3$, $R^4$, $A^2$, X, n and m are as defined in relation to formula (I) and Z represents a leaving group, with an activated form of a compound of formula (V):

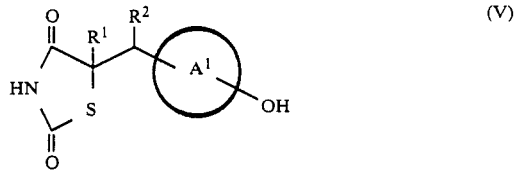

wherein $R^1$, $R^2$ and $A^1$ are as defined in relation to formula (I); and thereafter, if required, carrying out one or more of the following optional steps:
(i) converting a compound of formula (I) into a further compound of formula (I);
(ii) preparing a pharmaceutically acceptable salt of the compound of formula (I) and/or a pharmaceutically acceptable solvate thereof.

Suitably, Z represents a halogen atom, such as a chlorine or bromine atom, or a toluenesulphonyloxy or methanesulphonyloxy group.

A suitable activated form of a compound of formula (V) is a salted form as provided by a base such as sodium hydride.

The reaction between the compounds of formulae (IV) and (V) is conveniently carried out in an aprotic solvent, such as dimethylformamide, at any temperature providing a suitable rate of formation of the required product, suitably at ambient to elevated temperature such as in the range from 60° to 120° C. and preferably in the presence at a base.

A compound of formula (IV) may he prepared by reaction of an activated form of a compound of formula (VI):

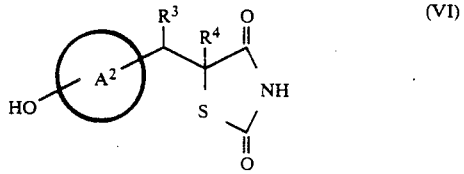

wherein $R^3$, $R^4$ and $A^2$ are as defined in relation to formula (I), with a compound of formula (VII):

$$Z^1-(CH_2)_nX(CH_2)_m-Z \qquad (VII)$$

wherein X, Z, n and m are as defined in relation to formula (IV) and $Z^1$ represents Z or a group or atom convertible thereto.

The reaction between the compounds of formula (VI) and (VII) may be carried out under analogous conditions to those used in the reaction between compounds of formulae (IV) and (V).

In one preferred aspect of the process for preparing a compound of formula (I), especially when $A^1 = A^2$, the compound of formula (IV) is not isolated and thus the compound of formula (VI) is reacted with the compound of formula (VII) in an appropriate stoichiometric ratio (at least 2:1) to provide a compound of formula (I); and thereafter, if required, carrying out one or more of the following optional steps:
(i) converting a compound of formula (I) into a further compound of formula (I);
(ii) preparing a pharmaceutically acceptable salt of the compound of formula (I) and/or a pharmaceutically acceptable solvate thereof.

Preferably in the compound of formula (VII), $Z^1$ represents Z.

A compound of formula (II) or (III), as appropriate, may be prepared by reacting a compound of formula (VIII):

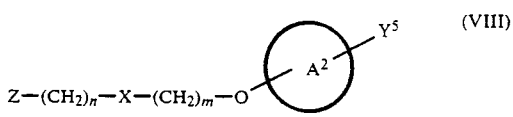

wherein X, Z, n and m are as defined in relation to formula (IV) and $Y^5$ represents the abovedefined $Y^1$ or $Y^3$ as appropriate, with an activated form of a compound of formula (IX):

wherein $A^1$ is as defined in relation to formula (I). and $Y^6$ represents the abovedefined Y or $Y^2$ as appropriate; and thereafter if required deprotecting a protected form of a —CHO group.

A compound of formula (VIII) may be prepared from an activated form of a compound of formula (X)

wherein $A^2$ and $Y^5$ are as defined in relation to formula (VIII), with the abovedefined compound of formula (VII).

A suitably activated form of a compound of formula (IX) or (X) is a salted form provided by a base such as sodium hydride.

The reactions between the compounds of formulae (VIII) and (IX) or (VII) and (X) are suitably carried out under the conditions described above for the reaction between compounds of formulae (IV) and (V).

The compounds of formulae (VII), (IX) and (X) are known compounds or are prepared according to methods used to prepare such compounds.

The compounds of formula (II) wherein Y and $Y^1$ both represent —CHO, are known compounds or they are compounds prepared by methods analogous to those used to prepare known compounds, for example those methods disclosed in Journal of Organic Chemistry, 26, 1961, 474–476.

The abovementioned conversion of a compound of formula (I) into a further compound of formula (I) includes the following conversions:

(a) reducing a compound of formula (I) wherein $R^1$ and $R^2$ together represent a bond into a compound of formula (I) wherein $R^1$ and $R^2$ each represent hydrogen; and (b) reducing a compound of formula (I) wherein $R^3$ and $R^4$ together represent a bond into a compound of formula (I) wherein $R^3$ and $R^4$ each represent hydrogen;

(c) where $R^1$ is hydrogen, converting $R^1$ to alkyl, aralkyl or aryl; and (d) where $R^4$ is hydrogen, converting $R^4$ to alkyl, aralkyl or aryl.

The conversion of a compound of formula (I) into a further compound of formula (I) may be carried out by using any appropriate conventional procedure.

A suitable reduction method for the abovementioned reductions (a) and (b) includes catalytic reduction or the use of a metal/solvent reducing system.

Suitable catalysts for use in the catalytic reduction are palladium on carbon catalysts, preferably a 10% palladium on charcoal catalyst; the reduction being carried out in a solvent, for example dioxan, suitably at elevated temperature.

Suitable metal/solvent reducing systems include magnesium in methanol.

Suitable methods for converting $R^1$ or $R^4$ from hydrogen into alkyl, aralkyl or aryl, in conversions (c) and (d), include conventional alkylation, aralkylation or arylation techniques, for example by reaction with a compound of formula (XI):

$$R^c\text{—}Z \qquad (XI)$$

wherein $R^c$ represents an appropriate alkyl, aralkyl or aryl group and Z represents a leaving group, such as a halogen atom for example an iodine atom.

The reaction with the compound of formula (IV) may be carried out in any suitable solvent, such as 1,2-dimethoxyethane at any temperature providing a convenient rate of formation of the required product, suitably at ambient temperature, and preferably in the presence of a base such as an alkali metal base, for example potassiuim amide in liquid ammonia.

It will be appreciated that in the abovementioned conversions (a), (b), (c) or (d) any reactive group in the compound of formula (I) would be protected, according to conventional chemical practice, where necessary.

Where appropriate the isomeric forms of the compounds of formula (I) and the pharmaceutically acceptable salts thereof may be prepared as individual isomers using conventional chemical procedures.

As mentioned above the compounds of the invention are indicated as having useful therapeutic properties:

The present invention accordingly provides a compound of formula (I), or a tautomeric form thereof and/or a pharmaceutically acceptable salt thereof and/or a pharmaceutically acceptable solvate thereof, for use as an active therapeutic substance.

Thus the present invention provides a compound of formula (I). or a tautomeric form thereof and/or a pharmaceutically acceptable salt thereof and/or a pharmaceutically acceptable solvate thereof, for use in the treatment of and/or prophylaxis of hyperglycaemia.

In a further aspect the present invention also provides a compound of formula (I), or a tautomeric form thereof and/or a pharmaceutically acceptable salt thereof and/or a pharmaceutically acceptable solvate thereof, for use in the treatment and/or prophylaxis of hyperlipidaemia.

As indicated hereinbefore the present invention also provides a compound of formula (I) or a tautomeric form thereof and/or a pharmaceutically acceptable salt thereof and/or a pharmaceutically acceptable solvate thereof, for use in the treatment of hypertension, cardiovascular disease and certain eating disorders.

A compound of formula (I), or a tautomeric form thereof and/or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of the general formula (I), or a tautomeric form thereof, or a pharmaceutically acceptable salt thereof, or a pharmaceutically acceptable solvate thereof, and a pharmaceutically acceptable carrier therefor.

As used herein the term 'pharmaceutically acceptable' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The present invention further provides a method for the treatment and/or prophylaxis of hyperglycaemia in a human or non-human mammal which comprises administering an effective, non-toxic, amount of a compound of the general formula (I), or a tautomeric form thereof and/or a pharmaceutically acceptable salt thereof and/or a pharmaceutically acceptable solvate thereof to a hyperglycaemic human or non-human mammal in need thereof.

The present invention further provides a method for the treatment of hyperlipidaemia in a human or non-human mammal, which comprises administering an effective, non-toxic, amount of a compound of formula (I), or a tautomeric form thereof and/or a pharmaceutically acceptable salt thereof and/or a pharmaceutically acceptable solvate thereof, to a hyperlipidaemic human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans, and/or the treatment and/or prophylaxis of hyperlipidaemic human, the compound of the general formula (I), or a tautomeric form thereof and/or a pharmaceutically acceptable salt thereof and/or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be adminstered by mouth, usually once or twice a day and in an amount in the range of from about 0.025 mg/kg to 25 mg/kg, for example 0.1 mg/kg to 20 mg/kg. Similar dosage regimens are suitable for the treatment and/or prophylaxis of hyperlipidaemia in non-human mammals.

The dosage regimens for the treatment of hypertension, cardiovascular disease and eating disorders will generally be those mentioned above in relation to hyperglycaemia.

In a further aspect the present invention provides the use of a compound of formula (I), or a tautomeric form thereof and/or a pharmaceutically acceptable salt thereof and/or a pharmaceutically acceptable solvate thereof, for the manufacture of a medicament for the treatment and/or prophylaxis of hyperglycaemia.

The present invention also provides the use of a compound of formula (I), or a tautomeric form thereof and/or a pharmaceutically acceptable salt thereof, and/or a pharmaceutically acceptable solvate thereof, for the manufacture of a medicament for the treatment and/or prophylaxis of hyperlipidaemia, hypertension, cardiovascular disease or certain eating disorders.

The following Procedures and Examples illustrate the invention but do not limit it in any way.

EXAMPLE 1

1,3-Bis-[4-[5-(2,4-dioxothiazolidinyl)methyl]phenoxy]-propane.

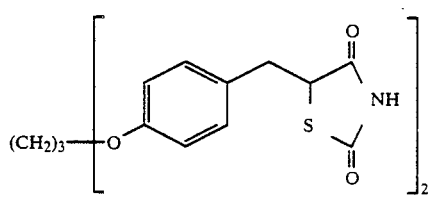

A suspension of 1,3-bis-[4-[5-(2,4-dioxothiazolidinyl)-methylene]phenoxy]propane (3.6 g) in dioxan (50 ml) was hydrogenated in the presence of 10% palladium on charcoal (3 g) at 100 p.s.i. of hydrogen with steam heating for 8 hours. The mixture was cooled to room temperature, filtered through diatomaceous earth and evaporated to dryness under reduced pressure. The title compound was obtained pure by crystallisation from methanol (MP 147°-8°)

$^1$H NMR δ (DMSO-d$_6$): 2.15-2.2 (2H, m); 3.0-3.35 (4H, complex); 4.15 (4H, t); 4.85 (2H, complex); 6.9 (4H, d); 7.2 (4H, d); 12.0 (2H, s, exchange with D$_2$O).

EXAMPLE 2

1,3-Bis-[4-[5-(2,4-dioxothiazolidinyl)methylene]phenoxy]propane

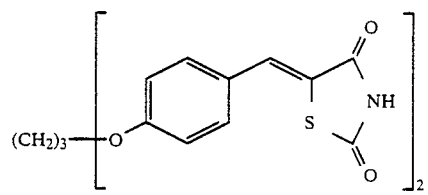

2,4-Thiazolidinedione (2.3 g) and 1,3-bis-[4-formylphenoxy] propane (2.8 g) were mixed in dry toluene (100 ml) in the presence of piperidinium acetate (catalytic) in a.Dean and Stark apparatus. The mixture was boiled under reflux for 5 hours, filtered hot and the precipitate was dried to give the title compound (MP. 296°-7° C.).

EXAMPLE 3

1,2-Bis[4-[5-(2,4-dioxothiazolidinyl)methyl]phenoxy]ethane.

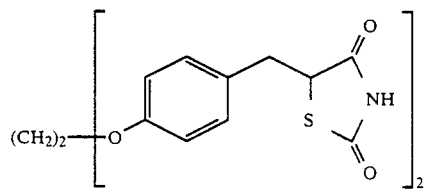

The title compound (MP 185°-6° C., methanol) was prepared from 1,2-bis-[4-[5-(2,4-dioxothiazolidinyl)-methylene] phenoxy] ethane (3.2 g) by an analogous procedure to that described in Example 1.

$^1$H NMR δ (DMSO-d$_6$) 3.0-3.25 (4H, complex); 4.1-4.2 (4H, t); 4.85 (2H, complex); 6.9 (4H, d); 7.2 (4H, d); 12.0 (2H, s, exchange with D$_2$O).

EXAMPLE 4

1,2-Bis-[4-[5-(2,4-dioxothiazolidinyl)methylene]phenoxy]ethane.

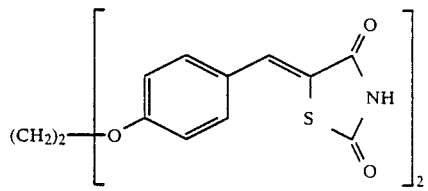

The title compound (MP >300° C.) was prepared from 2,4-thiazolidinedione (2.1 g) and 1,2-bis-(4-formylphenoxy) ethane (2.45 g) by an analogous procedure to that described in Example 2.

EXAMPLE 5

1,4-Bis-[4-[5-(2,4-dioxothiazolidinyl)methyl]phenoxy]-butane

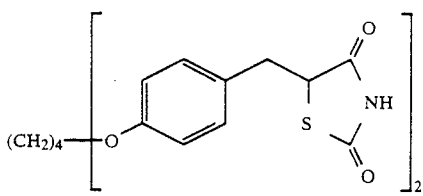

The title compound (MP 175°–7° C., MeOH) was prepared from 1,4-bis-[4-[5-(2,4-dioxothiazolidinyl)methylene]phenoxy]butane (6.0 g) by an analogous procedure to that described in Example 1.

$^1$H NMR δ (DMSO-d$_6$): 1.85 (4H, t); 3.0–3.3 (4H, complex); 3.9 (4H, t); 4.85 (2H, complex); 6.9 (4H, d); 7.2 (4H, d); 12.0 (2H, s, exchange with D$_2$O).

EXAMPLE 6

1,4-Bis-[4-[5-(2,4-dioxothiazolidinyl)methylene]-phenoxy] butane

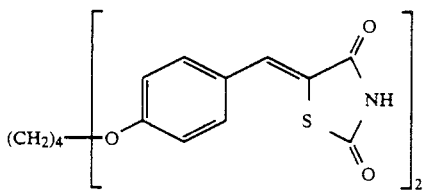

The title compound (MP 253°–5° C.) was prepared from 2,4-thiazolidinedione (4.68 g) and 1,4-bis-[4-formylphenoxy]butane by an analogous procedure to that described in Example 2.

EXAMPLE 7

1,5-Bis-[4-5-(2,4-dioxothiazolidinyl)methyl]phenoxy] pentane

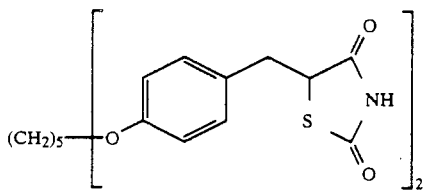

Sodium hydride (1.6 g; 60% dispersion in oil) was added in one portion to a solution of 5-[4-hydroxybenzyl]-2,4-thiazolidinedione (4.46 g) in dry dimethylformamide (50 ml) under nitrogen with stirring at room temperature. When the vigorous reaction ceased a solution of 1,5-dibromopentane (2.30 g) in dry dimethylformamide (20 ml) was added dropwise with stirring. On completion of the addition the mixture was heated to 80° C. and maintained at this temperature with stirring for 15 hours. After cooling the solution was added to iced 10% hydrochloric acid (200 ml). The solution was extracted with dichloromethane (3×150 ml), the combined organic extracts were washed with saturated brine (3×200 ml), dried (MgSO$_4$) and evaporated. The title compound (MP 143°–4° C., MeOH) was obtained following chromatography on silica-gel using 2% methanol-dichloromethane as eluent.

$^1$H NMR δ (DMSO-d$_6$): 1.4–1.9 (6H, complex); 3.0–3.35 (4H, complex) 4.0 (4H, t); 4.85 (2H, m); 6.85 (4H, d) 7.2 (4H, d); 12.0 (2H, s, exchange with D$_2$O).

EXAMPLE 8

1,6-Bis-[4-[5-(2,4-dioxothiazolidinyl)methyl]phenoxy]-hexane

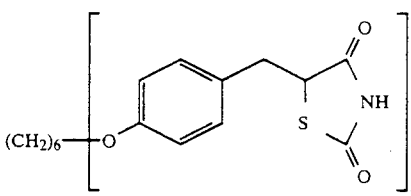

The title compound (MP 154°–5° C.; MeOH) was prepared from 1,6-bis-[4-[5-(2,4-dioxothiazolidinyl)methylene]phenoxy]hexane (5.4 g) by an analogous procedure to that described in Example 1.

$^1$H NMR δ (DMSO-D$_6$): 1.45 (4H, complex); 1.75 (4H, complex); 2.95–3.4 (4H, complex); 3.9–4.0 (4H, complex); 4.9 (2H, complex); 6.85 (4H,d); 7.2 (4H, d); 12.0 (2H, s, exchange with D$_2$O).

EXAMPLE 9

1.6-Bis-[4-[5-(2 4-dioxothiazolidinyl)methylene]phenoxy] hexane

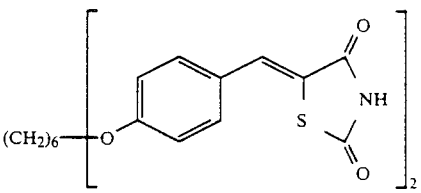

The title compound (MP 284°–6° C.) was prepared from 2,4-thiazolidinedione (6.1 g) and 1,6-bis-[4-formylphenoxy] hexane (8.5 g) by an analogous procedure to that described in Example 2.

EXAMPLE 10

2,2'-Bis[4-[5-(2,4-dioxothiazolidinyl)methyl]phenoxyl]-diethyl ether

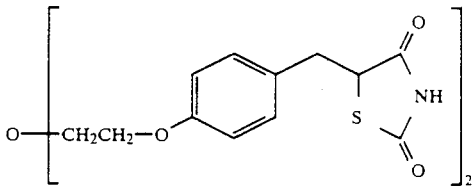

Sodium hydride (1.6 g;60% dispersion in oil) was added in one portion to a solution of 5-(4-hydroxybenzyl)thiazolidine-2,4-dione (4.46 g) in dry dimethylformamide (50 ml) under nitrogen with stirring at room temperature. When the vigorous reaction ceased a solution of 2,2'-dichloroethyl ether in dry dimethylformamide (15 ml) was added dropwise. The mixture was warmed to 80° C. and maintained at this temperature for 6 hours. After cooling the solution was added to iced water (250 ml) and the organic extracts were washed with saturated brine (3×250 ml), dried (magnesium sulphate) and evaporated to dryness. The title compound (MP 126°-7° C., MeOH) was obtained following chromatography on silica-gel in 2% methanol-dichloromethane and crystallisation.

$^1$H NMR δ (DMSO-d$_6$): 3.0-3.4 ( 4H,complex); 3.7-3.8 (4H, complex); 4.0-4.2 (4H, complex); 4.8-4.9 (2H, complex); 6.9 (4H, doublet); 7.2 (4H, doublet); 12.0 (2H,singlet,exchange with D$_2$O).

EXAMPLE 11

2,2'-Bis-[[4-[-(2,4-dioxothiazolidinyl)methyl]phenoxy]ethyl]methylamine.

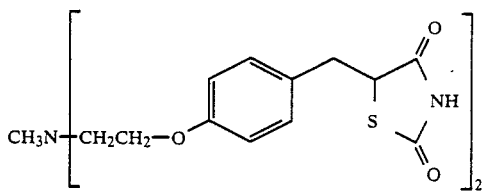

The title compound was obtained as a foam from 2,2'-bis-[[4-[5-(2,4-dioxothiazolidinyl)methylene]-phenoxy]ethyl]methylamine by an analogous procedure to that described in example 1.

$^1$NMR δ (DMSO-d$_6$): 2.4 (3H, s); 2.8 (4H, t); 3.0-3.4 (4H, complex); 4.05 (4H, t); 4.8 (2H, complex); 6.9 (4H, d); 7.2 (4H, d); 11.8-12.2 (2H, broad s, exchange with D$_2$O).

EXAMPLE 12

2,2'-Bis-[[4-[5-(2,4-dioxothiazolidinyl)methylene]-phenoxy]ethyl]methylamine.

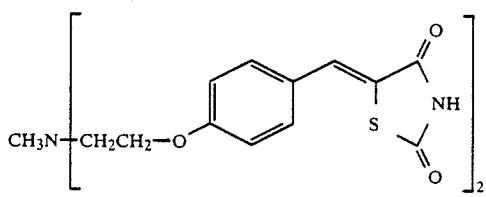

The title compound (MP 232° C.) was prepared from 2,2'-bis-[[4-formylphenoxy]ethyl]methylamine and 2,4-thiazolidinedione by an analogous procedure to that described in Example 2.

$^1$H NMR δ (DMSO-d$_6$): 2.5 (3H, s); 2.9-3.1 (4H, t); 4.2-4.4 (4H, t); 7.1 (4H, d); 7.5 (4H, d); 7.8 (2H, s).

EXAMPLE 13

2,2'-Bis-[[4-[5-(2,4-dioxothiazolidinyl)methyl]phenoxy]ethyl]amine hydrochloride monohydrate.

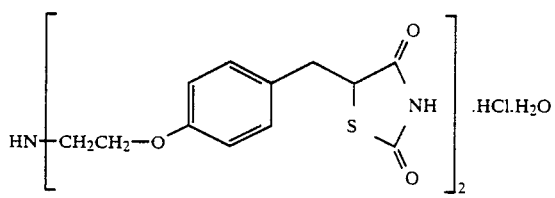

A mixture of N-carbobenzyloxy-2,2'-bis-[[4-[5-(2,4-dioxothiazolidinyl)methyl]phenoxy]ethyl]amine (5.6 g) in ethanol (120 ml) and hydrochloric acid (100 ml; 6M) was boiled under reflux for 24 hours. The cooled mixture was filtered and the precipitate was washed with ethyl acetate and water and dried under vacuum at 60° C. to give the title compound (MP 221° C.; Aq. Methanol).

$^1$H NMR δ (DMSO-d$_6$+TFA-d): 3.1-3.55 (4H, complex); 3.7-3.8 (4H, t); 4.3-4.5 (4H, t); 4.8 (2H, complex); 6.9 (4H, d); 7.25 (4H, d); 12.9 (6H, complex, exchange with D$_2$O).

EXAMPLE 14

N-Carbobenzyloxy-2,2'-bis-[[4-[5-(2,4-thiazolidinyl)methyl]phenoxy]ethyl]amine.

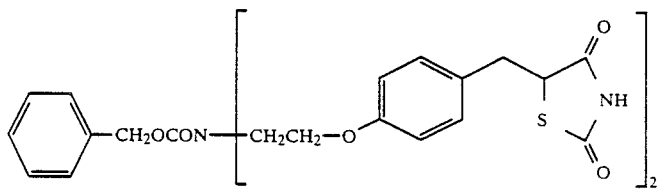

The title compound was obtained from 5-(4-hydroxybenzyl)thiazolidine-2,4-dione and N-carbobenzyloxy-2,2'-bis[methanesulphonyloxyethyl]amine by an analogous procedure to that described in Example 10.

$^1$H NMR δ (DMSO-d$_6$): 2.9-3.4 (4H, complex); 3.7 (4H, t); 4.1 (4H, t); 4.7-4.9 (2H, complex); 5.2 (2H, s); 6.8 (4H, d); 7.2 (4H, d); 7.4 (5H, s).

DEMONSTRATION OF EFFICACY OF COMPOUNDS

Obese Mice, Oral Glucose Tolerance Test

C57bl/6 obese (ob/ob) mice were fed on powdered oxoid diet. After at least one week, the mice continued on a powdered oxoid diet or were fed powdered oxoid diet containing the test compound. After 8 days on the supplemented diet all of the mice were fasted for 5 hours prior to receiving an oral load of glucose (3 g/kg). Blood samples for glucose analysis were taken 0, 45, 90 and 135 minutes after glucose administration and the results appear below as the percentage reduction in area under the blood glucose curve where test compound treated groups are compared with the control groups. 7 mice were used for each treatment.

| EXAMPLE NO: | LEVEL IN DIET ($\mu$mol kg$^{-1}$ of DIET) | % REDUCTION IN AREA UNDER BLOOD GLUCOSE CURVE |
|---|---|---|
| 1 | 300 | 46 |
| 3 | 100 | 16 |
| 5 | 100 | 27 |
| 7 | 100 | 20 |
| 8 | 100 | 14 |
| 10 | 100 | 28 |
| 11 | 100 | 17 |
| 13 | 300 | 23 |

Toxicology

No toxicological effects were indicated for any of the compounds of the invention in any of the abovementioned tests.

I claim:

1. A compound of formula (I):

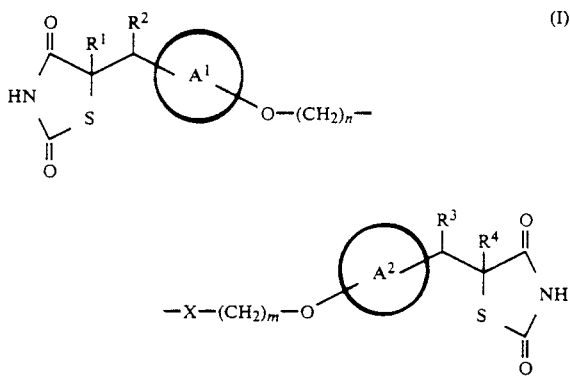

or a tautomeric form thereof and/or a pharmaceutically acceptable salt thereof and/or a pharmaceutically acceptable solvate thereof, characterized in that:

$R^1$ represents hydrogen or $C_{1-12}$ alkyl and $R^2$ represents hydrogen or $R^1$ and $R^2$ together represent a bond;

$R^3$ represents hydrogen and $R^4$ represents hydrogen or $C_{1-12}$ alkyl or $R^3$ and $R^4$ together represent a bond;

X represents a bond, >C=O, >CHOH, O, S or NR wherein R is a $C_{1-12}$ alkyl group;

n represents an integer 1, 2 or 3;

m represents an integer 1, 2 or 3 and $A^1$ and $A^2$ each independently represent a benzene ring having in total up to 5 substituents comprising up to 3 optional substituents selected from halogen, substituted or unsubstituted $C_{1-12}$ alkyl or $C_{1-12}$ alkoxy; and wherein optional substituents for the $C_{1-12}$ alkyl group are up to five, groups selected from halogen, $C_{1-12}$ alkyl, phenyl, $C_{1-12}$ alkoxy, halo-$C_{1-12}$-alkyl, hydroxy, amino, nitro, carboxy, $C_{1-12}$ alkoxycarbonyl, $C_{1-12}$ alkoxycarbonyl-$C_{1-12}$-alkyl, $C_{1-12}$ alkylcarbonyloxy, or $C_{1-12}$ alkylcarbonyl groups.

2. A compound according to claim 1, wherein $R^1$ and $R^2$ each represent hydrogen.

3. A compound according to claim 1, wherein $R^3$ and $R^4$ each represent hydrogen.

4. A compound according to claim 1, wherein X represents a bond.

5. A compound according to claim 1, wherein $A^1$ and $A^2$ each represent a benzene ring having no optional substituents.

6. A compound of formula (IA):

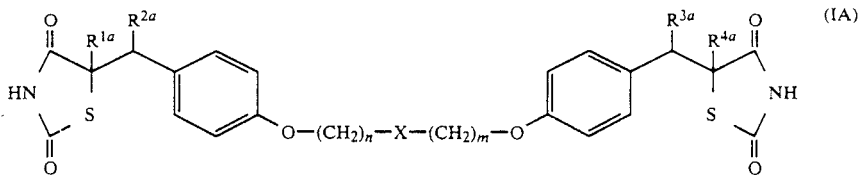

or a tautomeric form thereof and/or a pharmaceutically acceptable salt thereof and/or a pharmaceutically acceptable solvate thereof, characterised in that:

$R^{1a}$ and $R^{2a}$ each represent hydrogen or $R^{1a}$ and $R^{2a}$ together represent a bond;

$R^{3a}$ and $R^{4a}$ each represent hydrogen or $R^{3a}$ and $R^{4a}$ together represent a bond;

X represents a bond, >C=O or >CHOH;

n represents an integer 1, 2 or 3; and m represents an integer 1, 2 or 3.

7. A compound according to claim 1, selected from the group consisting of:

1,3-bis-[4-[5-(2,4-dioxothiazolidinyl)methyl]phenoxy]propane;

1,3-bis-[4-[5-(2,4-dioxothiazolidinyl)methylene]phenoxy]propane, 1,2-bis[4-[5-(2,4-dioxothiazolidinyl)methyl]phenoxy]ethane;

1,2-bis[4-[5-(2,4-dioxothiazolidinyl)methylene]phenoxy]ethane;

1,4-bis-[4-[5-(2,4-dioxothiazolidinyl)methyl]phenoxy]butane;

1,4-bis-[4-[5-(2,4-dioxothiazolidinyl)methylene]phenoxy]butane;

1,5-bis-[4-[5-(2,4-dioxothiazolidinyl)methyl]phenoxy]pentane;

1,6-bis-[4-[5-(2,4-dioxothiazolidinyl)methyl]phenoxy]hexane; and 1,6-bis-[4-[5-(2,4-dioxothiazolidinyl)methylene]phenoxy]hexane;

2,2'-bis[4-[5-(2,4-dioxothiazolidinyl)methyl]phenoxy]diethyl ether;

2,2'-bis-[[4-[-(2,4-dioxothiazolidinyl)methyl]phenoxy]ethyl]methylamine;

2,2'-bis-[[4-[5-(2,4-dioxothiazolidinyl)methylene]phenoxy]ethyl]methylamine;

2,2'-bis-[[4-[5-(2,4-dioxothiazolidinyl)methyl]phenoxy]ethyl]amine; and

N-carbobenzyloxy-2,2'-bis-[[4-[5-(2,4-thiazolidinyl)methyl]phenoxy]ethyl]amine; or a tautomeric form thereof and/or a pharmaceutically acceptable salt thereof and/or a pharmaceutically acceptable solvate thereof.

8. A pharmaceutical composition comprising a compound of the general formula (I) in accordance with claim 1, or a tautomeric form thereof, or a pharmaceutically acceptable salt thereof, or a pharmaceutically acceptable solvate thereof, and a pharmaceutically acceptable carrier therefor.

9. A method for the treatment and/or prophylaxis of hyperglycaemia in a human or non-human mammal which comprises administering an effective, non-toxic, amount of a compound of the general formula (I) in accordance with claim 1, or a tautomeric form thereof and/or a pharmaceutically acceptable salt thereof and/or a pharmaceutically acceptable solvate thereof to a hyperglycaemic human or non-human mammal in need thereof.

10. A method for the treatment of hyperlipidaemia in a human or non-human mammal, which comprises administering an effective, non-toxic, amount of a compound of formula (I) in accordance with claim 1, or a tautomeric form thereof and/or a pharmaceutically acceptable salt thereof and/or a pharmaceutically acceptable solvate thereof, to a hyperlipidaemic human or non-human mammal in need thereof.

* * * * *